Figure 1:
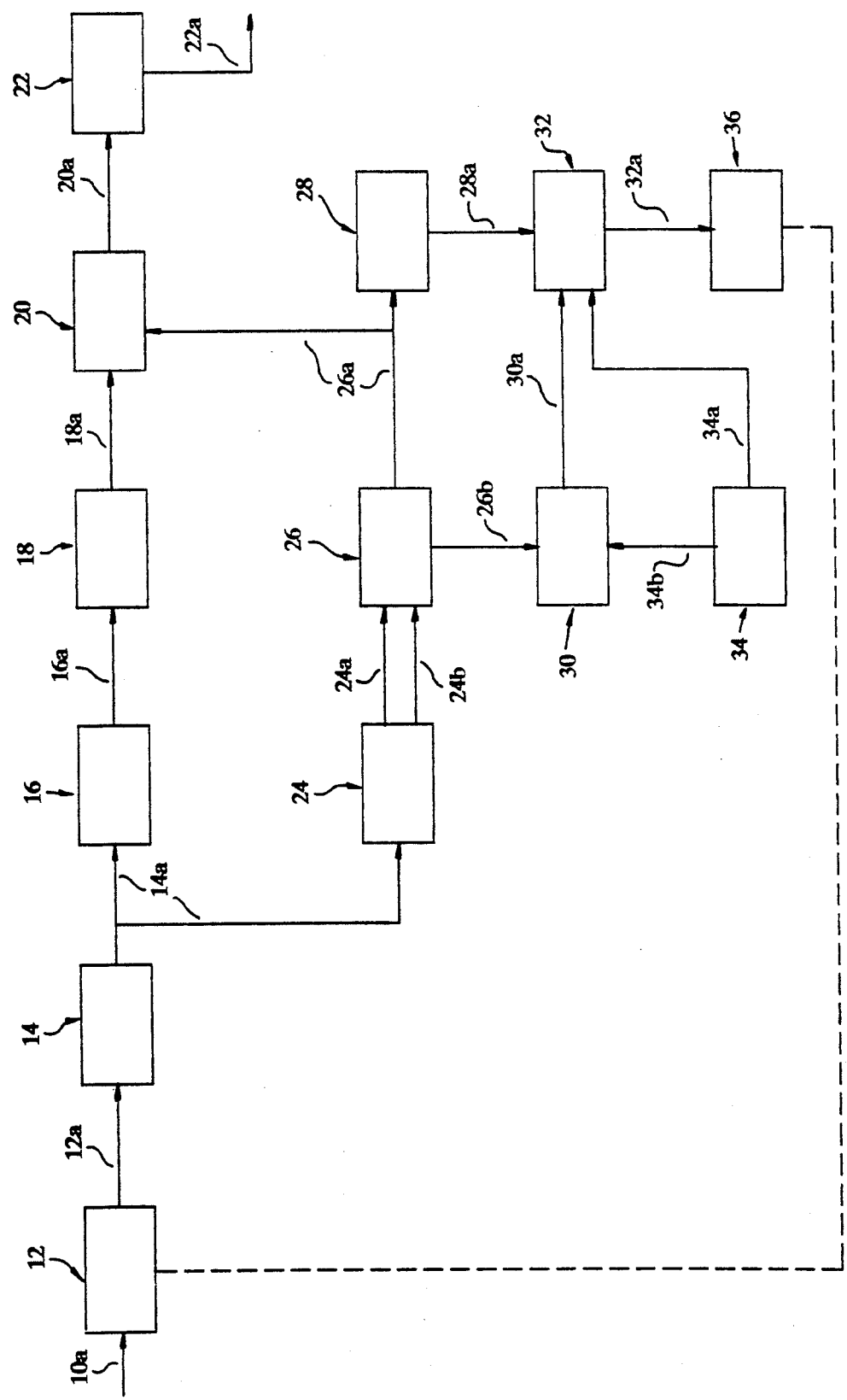

United States Patent [19]
Kirk

[11] Patent Number: 5,206,519
[45] Date of Patent: Apr. 27, 1993

[54] CONSTITUENT CONCENTRATION INDICATOR WITH A DIFFERENTIATOR MEANS AND A SIGNAL CONDITIONING MEANS

[75] Inventor: David Kirk, Calgary, Canada

[73] Assignee: Galvanic Analytical Systems Ltd., Alberta, Canada

[21] Appl. No.: 848,668

[22] Filed: Mar. 9, 1992

[51] Int. Cl.$^5$ .................................................. G01N 21/00
[52] U.S. Cl. ...................................... 250/565; 250/573
[58] Field of Search ............... 250/564, 565, 573, 339, 250/341, 343, 345, 214 R, 214 A; 356/346, 410, 434, 436, 448

[56] References Cited

U.S. PATENT DOCUMENTS 4,054,384 10/1977 Hawes ................................. 250/345
4,127,780 11/1978 Kimbell ................................ 356/448

Primary Examiner—David C. Nelms
Assistant Examiner—Que T. Le

[57] ABSTRACT

The Rolling Average Rate Read Indicator and Method detects the presence of a particular constituent in either a solid, liquid or gas and returns a rapid and accurate measurement of the concentration of the constituent. The Indicator is comprised of a sensor (12) containing a stepper motor (36) driven tape impregnated with a chemical substance reactive to a particular constituent. Discoloration of the tape occurs in the presence of the constituent and this discoloration is converted to an electrical signal which is indicative of the rate of change in the chemical reaction taking place and is linear for some portion of time. The signal is differentiated (16) and the resultant differentiated signal is indicative of the arithmetic mean of a plurality of instantaneous values taken at intervals during the linear portion of the reaction. The extent of the reaction as evidenced by the level of the sensor output signal is continuously monitored and compared (26) to a known value. If the sensor (12) output signal exceeds that of the known value the differentiated signal is transferred to a display device (22), the stepper motor (36) is activated and the sensor (12) tape is advanced in preparation for the receipt of a fresh sample. The tape advances only if a reaction has occurred. Optionally, the sensor (12) tape may be advanced at predetermined periodic intervals under the control of a timed override (30) or, at any time, by a manual override (34).

22 Claims, 4 Drawing Sheets

CONSTITUENT CONCENTRATION INDICATOR WITH A DIFFERENTIATOR MEANS AND A SIGNAL CONDITIONING MEANS

BACKGROUND—FIELD OF THE INVENTION

The invention relates to the detection and measurement of various constituents in liquids, solids and gases.

BACKGROUND—DESCRIPTION OF THE PRIOR ART

The need to accurately and reliably determine the various constituents of materials is well known and has been, and continues to be, the subject of much research. Within the oil and gas industry, for example, the need to determine the total sulfur content of hydrocarbon streams has been a focal point for the application of inventive ingenuity for over fifty years and new and improved methods and devices continue to emerge; each designed to enhance both the rapidity with which detection and measurement occur and the overall accuracy of the measurements obtained.

One such device, and upon which the present invention is an improvement, was first disclosed in U.S. Pat. No. 2,232,622 to Moses Et. Al. (1941) and consists of motor driven reels containing paper tape, impregnated with chemical substances known to react to various constituents such as hydrogen sulfide or carbon monoxide. The tape is enclosed in a substantially sealed housing and either periodically or continuously advanced such that, at any given time, a clean portion of tape is exposed to a metered, gaseous sample.

When exposed to a sample containing a reactive constituent a discoloration of the chemically impregnated tape occurs and the degree of the discoloration is measured as an electrical signal representing the difference in the amount of light reflected off the stained tape as compared to the amount of light reflected off an unstained portion of the tape. The magnitude of the electrical signal thus produced is a measurement of the absolute concentration of the particular constituent.

Over the years many workshop improvements have been made to the basic device disclosed in U.S. Pat. No. 2,232,622. For example, the means by which a zero reference is obtained has been subjected to many changes, as has the production and quality of the tape itself. The tape drive mechanism has seen many improvements and various methods have been employed to enable the gas sample to flow across the surface of the tape rather than through it.

While such improvements contibuted to the general reliability and performance of the device of U.S. Pat. No. 2,232,622, the basic underlying method of obtaining a measurement of constituent concentration remained unchanged, i.e., the device provided an absolute indication of constituent concentration and suffered all the shortcomings inherent with this method of measurement.

The need to provide a continuous zero reference base, free from drift is but one example of a disadvantage of the above mentioned device, as is the fact that an undesirable amount of time is required for saturation of the tape to full discoloration and the obtaining of a measurement.

In an attempt to address these shortcomings, inventors thereafter developed alternate methods of obtaining constituent measurements utilizing the Moses device. One such device disclosed in U.S. Pat. No. 4,127,780 to Kimbell (1978) reveals a method whereby the rate of change of the tape discoloration forms the basis for the constituent concentration measurement. This method is based upon the correct premise that the rate at which the tape discoloration occurs is linear for at least some small portion of time. The anticipated result of this method is a faster read rate and the elimination of the need for a stable zero reference.

While conceptually an improvement over an absolute measurement system, the Kimbell system nevertheless suffers several serious shortcomings. The electrical and electronic control circuits as disclosed by Kimbell and placed into commercial service, have been shown to be susceptible to transient electrical noise, resulting in the triggering of false alarms. Such alarms can lead to unnecessary plant shutdowns for up to eight hours, at a cost which may range as high as $25,000 per hour.

In addition, transient anomalies occuring during the linear portion of the rate increase can be interpreted by the Kimbell device as a true measurement which, in turn, may lead to an inaccurate reading.

The fact that the Kimbell device advances the tape at regular, periodic intervals (typically 2.5 minutes) whether or not staining has occurred, coupled with the use of a heavily geared, asynchronous drive motor which is incapable of precise control over the amount of tape advancement, leads to the replacement of tape with unnecessary frequency and hence, increases maintenance time and costs as well as slowing the overall response time required to obtain a valid reading.

The constituent indicators heretobefore known suffer, then, from a number of disadvantages:

(a) They require a stable zero reference.
(b) They are susceptable to transient electrical noise.
(c) They are prone to trigger false alarms.
(d) Their inability to distinguish transient anomalies can lead to false measurements.
(e) They cannot precisely regulate the amount of tape advance.
(f) They advance tape whether staining has occured or not.
(g) They require excessive maintenance.

OBJECTS AND ADVANTAGES

Accordingly, several objects and advantages of the present invention are:

(a) To provide a rate read indicator which obviates the need for a stable zero reference.
(b) To provide a rate read indicator which is substantially immune to transient electrical noise.
(c) To provide a rate read indicator which is substantially to triggering false alarms.
(d) To provide a rate read indicator capable of recognizing and ignoring transient anomalies and returning a substantially accurate reading at all times.
(e) To provide a rate read indicator capable of precisely regulating the amount of tape advance.
(f) To provide a rate read indicator which advances tape only if staining has occurred or, at the discretion of the operator.
(g) To provide a rate read indicator requiring reduced maintenance.

Further objects and advantages are to provide a rate read indicator wherein the response speed with which readings are obtained increases with increasing concentrations of the reactive constituent and is reliable, field servicable and intrinsically safe regardless of operating environment. Still further objects and advantages will become apparent from a consideration of the ensuing description and drawings.

DRAWING FIGURES

FIG. 1. shows a functional block diagram representative of the indicator.

Figure 2:
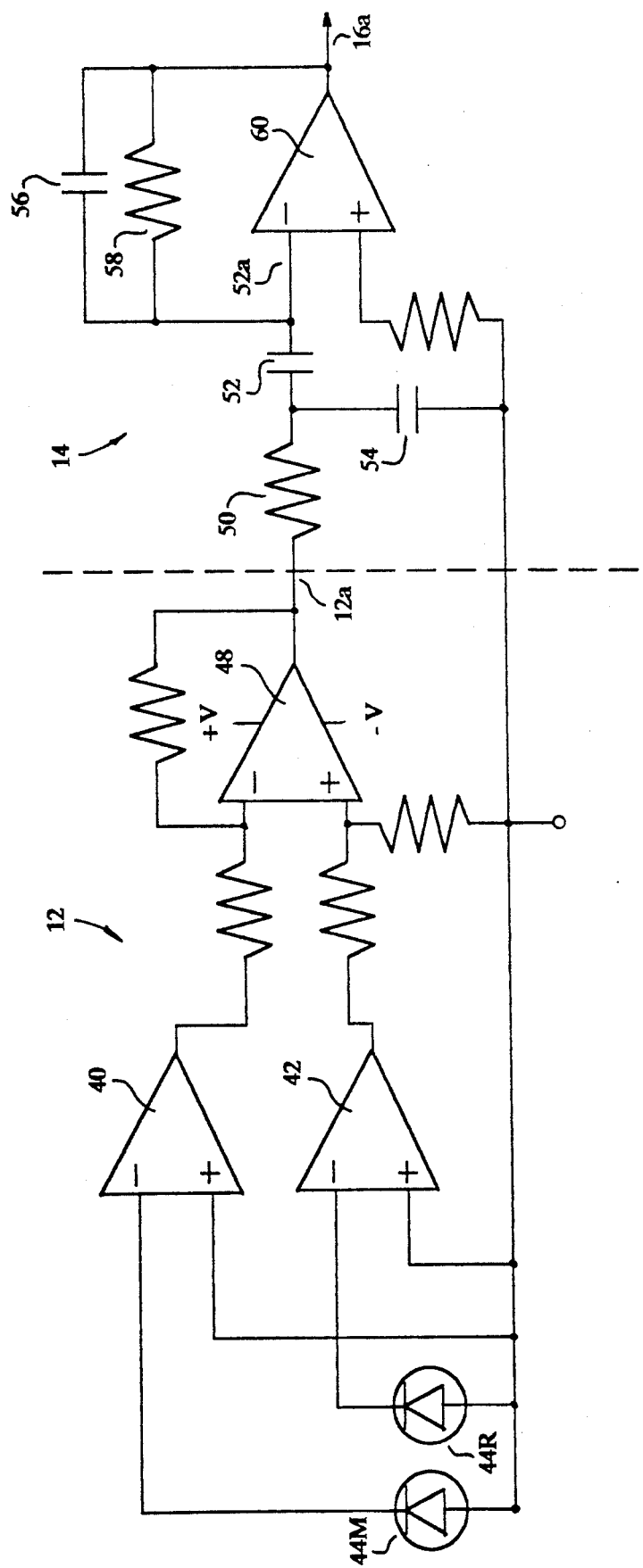

FIG. 2. shows a circuit diagram of the sensor and differentiator blocks.

Figure 3:
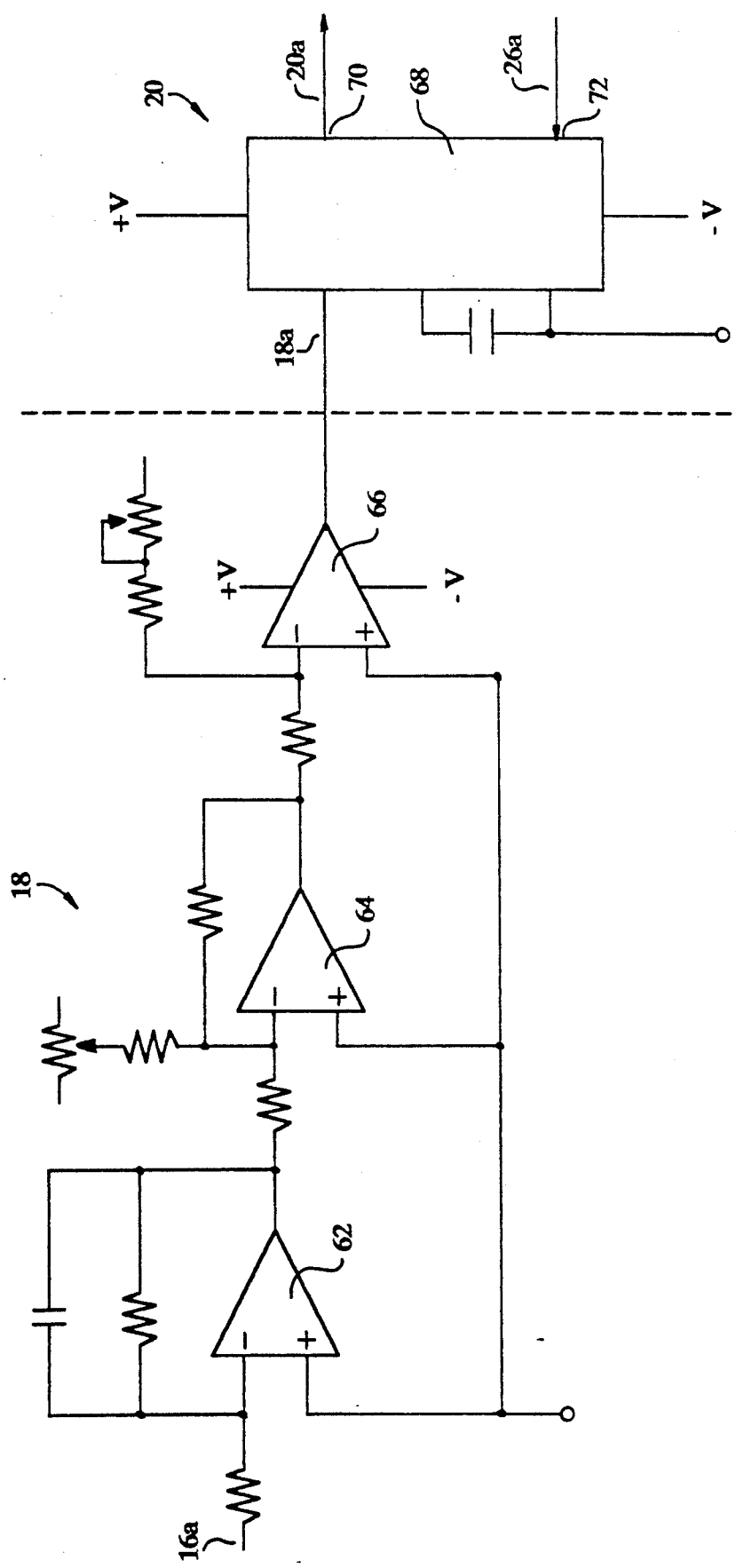

FIG. 3. shows a circuit diagram of the signal conditioning and sample and hold blocks.

Figure 4:
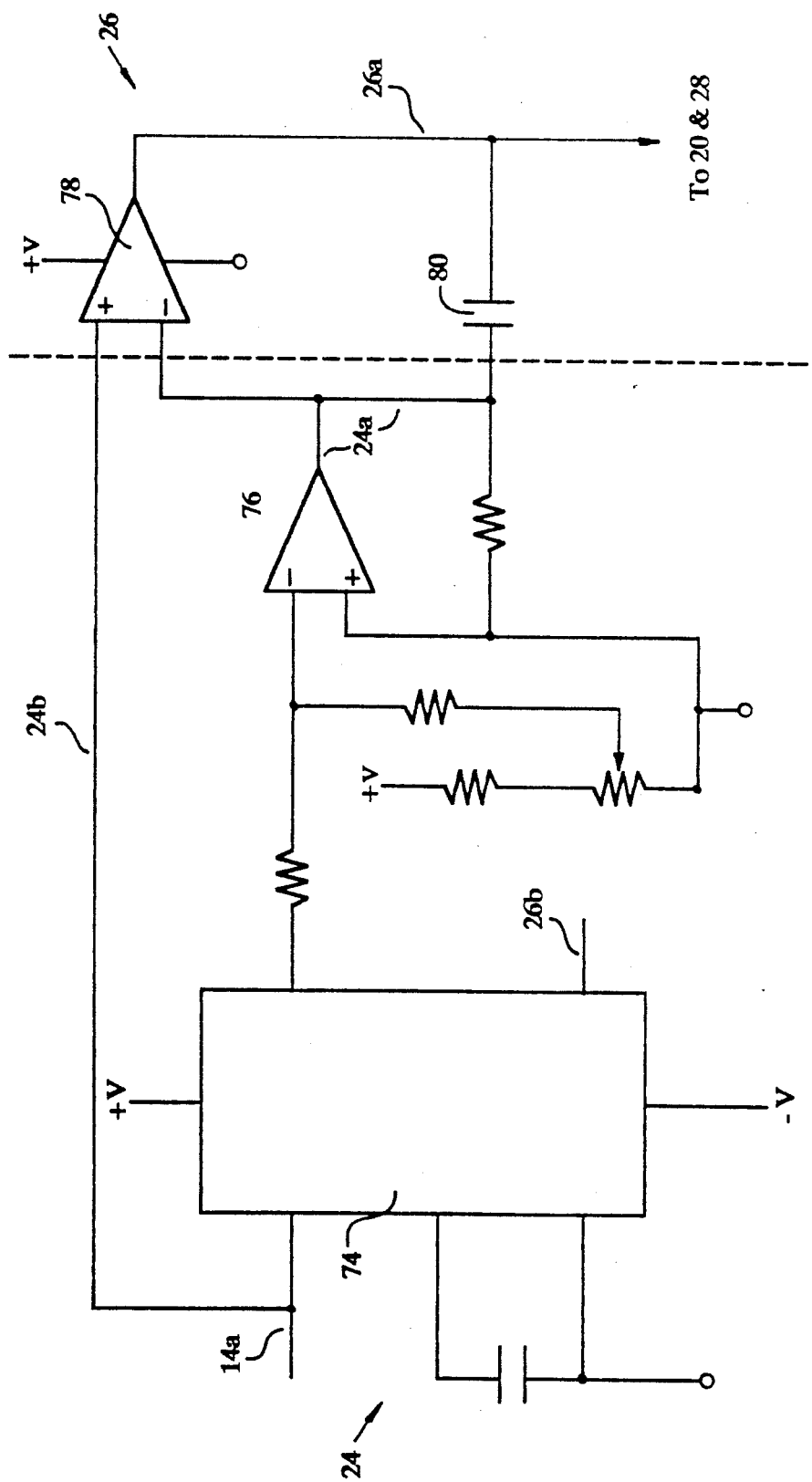

FIG. 4. shows a circuit diagram of the signal conditioning and comparator blocks

DESCRIPTION—FIGS. 1 TO 4

Although it is clear from the disclosure of Moses Et. Al., that the inventors anticipated the use of their invention for the detection and measurement of various constituents, they generally confined their description to the detection and measurement of hydrogen sulfide in gaseous samples by means of paper tape impregnated with lead acetate. For purposes of both clarity and continuity, then, and without limiting the scope of the present invention, the present disclosure, shall do likewise.

The present method of obtaining an accurate and rapid measurement of hydrogen sulfide in sample gases is based upon the premise that the reactive staining of the sensor tape is linear for at least some portion of time and that the ability to determine the rate of change of tape staining over this linear time portion can provide an accurate measurement of the absolute concentration of hydrogen sulfide in the sample gases. Unlike the "straight line" measurement method employed by the prior art and susceptable to transient anomalies and the attendant introduction of error, the measurement method of the present invention utilizes what may best be described as a "rolling average," whereby the end measurement obtained is the arithmetic mean of a relatively large number of periodic measurements taken over the length of the linear portion of the rate of change.

The essential difference between the measurement method of the present invention and that of the prior art may best be illustrated by the following example:

Example A. The increasing linear slope representing the change in concentration of hydrogen sulfide has the values of; 0.5 millivolts (mv) for 0.2 milliseconds (ms), 0.6 mv for 0.3 ms, and 0.7 mv for 0.3 ms and—perhaps as a result of transient electrical noise—an anomolous voltage spike of 1.2 mv for 0.05 ms.

The measurement method of the prior art will return a concentration reading in a direct relationship to the 1.2 mv aberation.

The measurement method of the present invention will return a concentration reading in a direct relationship to the arithmetic mean of the sum of the individual readings thus;

$$\Sigma fX/\Sigma f$$

Where
f=frequency of each occurence and
X=the value of each occurence.
Substituting values gives, 0.55/0.85=0.65 mv.

It can be seen, then, that the measurement method of the present invention is substantially immune to the effects of transient anomalies and thus provides a consistently accurate measurement.

Referring to FIG. 1., it may be seen that a metered sample of test gas 10a is introduced to a sensor 12 whereupon the chemically impregnated tape discolors if hydrogen sulfide is present in the sample 10a. The discoloration is interpreted as an electrical signal 12a which is proportional to the magnitude of the discoloration and is passed to a low pass filter 14 whereby any high frequency transient noise present in the signal 12a is blocked.

The output electrical signal of the low pass filter 14 is, in turn, input to a differentiator 16. The differentiator 16 provides a differentiated electrical signal 16a as an input signal to signal conditioning circuits 18 which perform additional amplification of the input signal 16a such as to raise the magnitude of the signal 16a to a level sufficient to ultimately drive a display 22, as well as providing means for span and null adjustment.

The output electrical signal 18a of the signal conditioning 18 passes to a sample and hold 20 where the signal 18a is retained until such times as the sample and hold 20 receives an appropriate electrical signal 26a from a comparator 26 to initiate the transfer of signal 20a from the sample and hold 20 to the display 22.

The transfer of the signal 20a from the sample and hold 20 to the display 22 is controlled by the output signal 26a of the comparator 26 which operates in the following manner: The low pass filter 14 output signal 14a, in addition to passing to the differentiator 16, is routed to the input of the signal conditioning circuitry 24 which is comprised of various electronic components interconnected in such a manner as to provide dual electrical output signals 24a and 24b, wherein the signal 24a is the sum of a zero reference voltage level (white tape), any offset voltage level present, i.e., any voltage level representative of a deviation around the zero reference level and a predetermined voltage level (nominally 0.5 volts), while the signal 24b is substantially equal in magnitude to the input signal 14a such that, when the magnitude of the signal 24b exceeds that of the signal 24a, the comparator 26 is "triggered" and generates a digital output signal 26a, thus initiating transfer of the signal 20a to the display 22.

In addition to passing to the sample and hold 20, the comparator 26 output signal 26a is routed to a delay 28. The electrical output signal 28a of the delay 28 is substantially equal in magnitude to the comparator 26 output signal 26a but lags the signal 26a by a predefined time period equal to the signal propagation time through the electronic components comprising the delay 28 such that the sequence of events is to first initiate transfer of the signal 20a to the display 22 and then activate a stepper motor 36.

The output signal 28a of the delay 28 passes to the input of a motor control 32 which, in turn, initiates rotation of the stepper motor 36 via electrical signals 32a. The rotation of the stepper motor 32 advances the chemically impregnated tape of the sensor 12 by a precise, predetermined amount in readiness for the next test sample 10a.

In the event that the magnitude of the signal conditioning 24 output signal 24b does non exceed the signal conditioning 24 output signal 24a for a predetermined time period as established by a timed override 30 and monitored via the electrical signal 26b, then the timed override 30 will "time out" and "trigger" the motor control 32 via the electrical signal 30a. The stepper motor 36 runs and the sensor 12 tape is advanced.

The sensor 12 tape may be advanced at any time by activation of a manual override 34 which outputs an electrical signal 34a to the motor control 32 that, in turn, activates the stepper motor via the signal 32a, and the electrical signal 34b to the timed override 30, initializing the timed override 30 to a "start time" condition.

It will be understood that the display 22 input signal 20a is a differentiated, amplified signal which is indicative of the rate of change of the concentration of hydrogen sulfide in the test sample gas 10a and that the method of measurement is in accordance with that described above while the display 22 output signal 22a may be used to activate alarms, chart recorders or other electrical devices as required.

Since the signal conditioning 24 output signal 24b is substantially equal in magnitude to the input signal 14a and the input signal 14a is proportional to the degree of discoloration of the chemically impregnated tape, then, the comparator 26 output signal 26a is indicative of the absolute tape discoloration. In the event that the magnitude of the signal conditioning 24 output signal 24b does not exceed the signal conditioning 24 output signal 24a, then the comparator output signal 26a will not occur and the sensor 12 tape will not be advanced until such times as the timed override 30 "times out". In this fashion, sensor 12 tape advance occurs in direct response to either the "triggering" of the comparator 26 as a result of tape discoloration OR "timing out" of the timed override 30, OR activation of the manual override 34.

The sensor 12 of the present invention is substantially the same as that first disclosed in U.S. Pat. No. 2,232,622 to Moses Et Al. (1941), wherein hydrogen sulfide reacts with a periodically or continuously advancing lead acetate impregnated tape which discolors in proportion to the level of concentration of hydrogen sulfide.

The degree of discoloration of the tape is converted to an electrical signal by means of the detection and measurement of light reflected off the stained tape as compared to light reflected off an unstained portion of tape. The overall manner of operation of the Moses device is well understood by those skilled in the art, therefore, no detailed description of such operation is herein provided, excepting in those areas where the present invention deviates from the preferred embodiment as disclosed by Moses Et Al.

As shown in FIG. 2, the means for converting tape discoloration to an electrical signals is accomplished by amplifiers 40 and 42, reference photodiode 44R, measurement photodiode 44M, an electrical power source, and a light source (not shown) powered by a constant current supply (not shown).

An imbalance in the photocurrent flow through the diodes 44R and 44M caused by a difference in reflected light to the reference diode 44R and the measurement diode 44M results in the signal 12a as the output of a difference amplifier 48. Signal 12a is conducted through a resistor 50 to a differentiating capacitor 52 which capacitor 52 responds only to changes in the signal 12a and a differentiated signal 52a passes to the inverting input of an amplifier 60. The resistor 50 sets the low frequency cutoff frequency while a feedback resistor 58 establishes the closed loop gain of the amplifier 60. Capacitor 56 acts as a low pass filter by reducing the amplifier 60 high frequency gain and ultimately the high frequency cutoff frequency. The combination of the resistor 50 and the capacitor 52 establishes the time constant over which measurement is taken—generally, this time constant is small compared to the input interval.

The output of the amplifier 60 is thus, an amplified, differentiated signal 16a which passes to the signal processing circuitry 18, detailed in FIG. 3., wherein the signal 16a is further amplified by an amplifier 62 and its associated biasing resistors before passing to an additional amplifier 64. In the event no staining of the lead acetate tape has occured, then, input offset voltage adjustment means are provided at the amplifier 64 to correct for inherent unbalance in the amplifier 64 and all prior amplifiers, i.e., 62,60 and 48.

The final stage of the signal conditioning circuitry consists of an amplifier 66 and its associated biasing resistors and includes a means for adjustment of span. The signal conditioning circuitry 18 output signal 18a is conducted to the sample and hold 20 which is comprised of an integrated circuit (IC) 68 and associated electronic components, interconnected in a standard configuration and well known to those skilled in the art. Signal 20a is available at the OUT port 70 of the IC 68 and is transferred to the display 22 upon receipt of the appropriate control signal 26a from the comparator 26 at the HOLD port 72 of the IC 68.

The display 22 of the preferred embodiment of the present invention is a standard, four digit, seven segment, vacuum fluorescent display such as are readily available from Omron Ltd., and other display manufacturers.

Signal conditioning circuitry 24, as shown in FIG. 4., is comprised of an IC 76 interconnected in a standard manner well known in the art, such as to provide a zero reference base (white tape), a method of compensating for any deviation from the zero reference (White tape plus offset) and a preset reference point of 0.5 volts nominal. The output signal of the IC 76 is conducted to one input of the comparator 26 as signal 24a and also combines with comparator 26 output signal 26a via a coupling capacitor 80. The second signal 24b to the comparator 26 is tapped off the signal conditioning 24 and input to the comparator 26 substantially unchanged. The comparator 26 consists of an integrated circuit 78, such as is known within the art and connected, in circuit, in standard fashion.

The time frame for the delay 28 is established as the amount of time for the signal 26a from the comparator 26 to propagate through two, standard, digital logic gates, connected in series. The preferred embodiment utilizes standard invertor gates such that the delay 28 input signal 26a emerges substantially unchanged as output signal 28a and is conducted to the motor control 32 which consists of a standard, stepper motor control, integrated circuit well known to those skilled in the art.

In response to the input signal 28a, the stepper motor control 32 passes the signal 32a to the stepper motor, which is of any convenient type and readily available. The receipt of the signal 32a by the stepper motor 36 causes the stepper motor 36 shaft to rotate through a set number of degrees as determined by the nature of the signal 32a from the motor control 32. The output shaft of the stepper motor 36 is mechanically linked to a tape "take up" reel of the sensor 12 and thus advances the tape of sensor 12 in preparation for a fresh gas test sample 10a.

The times override 30 consists of a standard timing integrated circuit and associated electronic components, interconnected in a conventional fashion and well known within the art, such as to provide either a count up or count down delay which is self initializing following "time out", or may be re-initialized by triggering of the comparator 26 via signal 26b, or, via signal 34b by activation of the manual override 34 which consists of a normally open, single pole, momentary push button switch of conventional design.

SUMMARY, RAMIFICATIONS AND SCOPE

Accordingly, the reader will see that the rolling average, rate read indicator and method of the present invention can be used to provide accurate, fast and reliable measurements of the concentration of hydrogen sulfide in sample gases. This is accomplished by taking the arithmetic mean of the linear portion of the rate of change of the reaction of the hydrogen sulfide with lead acetate impregnated tape. Furthermore, the rolling average read rate indicator and method has the additional advantages over the prior art in that it provides for an increased response time in the acquisition of valid measurements with increasing concentrations of the reactive constituent;

it reduces the frequency of tape replacement and thus reduces maintenance time and cost;

it utilizes solid state components throughout for control purposes, thereby reducing the risk of electrical arcing. Such arcing may be highly undesirable in certain hazardous environmental conditions;

it operates, for the most part, with low voltage direct current, thus reducing overall power consumption and the risk of shock to both service personnel and operators;

it is substantially immune to transient electrical noise and thus less prone to trigger false alarms than the prior art; and it is relatively simple and inexpensive to manufacture, utilizing well known and well understood production technologies and techniques.

Although the above description contains many specifications, these should not be construed as limiting the scope of the invention but as merely providing illustrations of the presently preferred embodiment of this invention. For example, a variety of different constituents may be detected and accurately measured by impregnating the sensor tape with chemical substances with which a particular constituent will react.

While the above description contemplates the use of the present invention in the measurement of hydrogen sulfide in a gaseous sample it is well within the scope of the present invention to also measure constituent concentrations in liquids and solids. For example, a liquid hydrocarbon sample may be converted to gas and reacted with hydrogen to convert various sulfur compounds, contained within the gas, to hydrogen sulfide. The hydrogen sulfide concentration may then be measured in the manner described herein. This method of converting sulfur compounds to hydrogen sulfide by hydrogenation is well known within the art and has been the subject of much research, the results of which are readily available in scientific publications dating back to the early 1960's. Solids, likewise, may first be converted to a gaseous state by pyrolysis and the resultant gas constituents measured as described herein.

The nature of the solid state electronics of the preferred embodiment are such that the present invention may be considered as a system comprised of functional blocks. There exist many different ways in which electronic components may be interconnected in order to achieve the functional results contemplated herein. For example, the functions of differentiation, timing control, motor and display control etc., may be readily achieved using a microprocessor running under the control of appropriate software.

The use of a timed override is entirely optional and is shown herein for purposes of illustration only. Whether or not such an override is included will be dictated more by commercial considerations than technical considerations.

Thus the scope of the present invention should be determined by the appended claims and their legal equivalents, rather than by the examples given.

I claim:

1. An instrument for the detection and measurement of a constituent concentration in liquid, solid and gaseous samples comprising:

detection means for detecting the presense of a particular constituent in a sample and providing an electrical output signal indicative of the constituent concentration wherein said electrical output signal has a linear component;

filtering means wherein undesirable attributes of said electrical output signal are blocked;

differentiator means wherein said linear component of said electrical output signal is differentiated and the differentiated signal is indicative of the average magnitude of increase in concentration of said constituent in said sample and hence the absolute concentration of said constituent in said sample;

signal conditioning means wherein said differentiated signal is manipulated in preparation for further use and the manipulated signal is proportional to said differentiated signal;

timing control means wherein the timing of the re-initialization of said detection means in preparation for the receipt of a new sample is determined; and display means for providing visual reporting of said manipulated signal.

2. The structure set forth in claim 1 wherein said detection means is comprised of reel mounted paper tape impregnated with a chemical substance reactive to a particular constituent.

3. The structure set forth in claim 2 further including a precision driving means to advance said tape by exact predetermined amounts.

4. The structure set forth in claim 2 wherein said precision driving means consists of a stepper motor.

5. The structure set forth in claim 2 further including transductance means for the conversion of said constituent reaction with said tape to an electrical signal.

6. The structure set forth in claim 2 wherein said transductance means is comprised of a constant current light source, dual transimpedance amplifiers with matched semiconductors responsive to light and an amplification means electrically connected to provide difference mode gain.

7. The structure set forth in claim 1 wherein said differentiator means is comprised of an amplification means and passive electronic components interconnected in an electrical circuit to provide the mathematical function of differentiation.

8. The structure set forth in claim 1 wherein said signal conditioning means is comprised of active and passive electronic components interconnected to provide amplification, input offset null adjustment, span adjustment and sample and hold functions.

9. The structure set forth in claim 1 wherein said timing control means is comprised of electronic circuits interconnected to provide a zero base reference indicative of an unreacted tape and to electrically compensate for deviations around said zero base reference.

10. The structure set forth in claim 9 further including electronic circuits interconnected to provide a predetermined voltage level summed with said zero reference and said deviations around said zero reference base.

11. The structure set forth in claim 9 further including comparison means wherein the sum of said zero reference base and said deviations around said zero reference base and said predetermined voltage level is compared with said electrical signal from said detection means to establish whether said reaction between said tape and said constituent has occurred and to determine the extent of said reaction in order to determine if said tape should be advanced in preparation for the receipt of a fresh sample.

12. The structure set forth in claim 9 further including motor control means wherein said stepper motor is rotated through a predetermined number of degrees in response to the electrical signal produced by said comparison means.

13. The structure set forth in claim 9 further including a timed override means wherein said tape is advanced at predetermined periodic intervals regard less of the electrical status of said comparison means.

14. The structure set forth in claim 9 further including a manual override means wherein said tape is advanced regardless of the status of said comparison means and said timed override means.

15. The structure set forth in claim 1 wherein said display means consists of a multidigit numeric digital electronic display.

16. The structure set forth in claim 15 further including signal output means to derive downstream electrical and electronic devices.

17. A constituent concentration indicator for the determination of various constituents in materials comprising;

transducing means wherein the reaction of a particular constituent with a chemically impregnated tape is converted to an electrical output signal the magnitude of which changes with time, is linear over some portion of said time and is indicative of the rate of reaction of said constituent with said tape;

signal conversion means wherein said electrical signal from said transducing means is differentiated and the differentiated signal is indicative of the arithmetic mean of a plurality of instantaneous values taken at intervals during said linear portion of said rate of change;

conditioning means wherein said differentiated signal is amplified, captured and held prior to transfer to a display; and comparison means wherein the absolute degree of said reaction is expressed as an electrical signal and compared to a known threshold level which if exceeded triggers said comparison means to initiate the transfer of said differentiated signal to said display and advance said tape in preparation for receipt of a new sample.

18. The structure set forth in claim 17 wherein said transducing means is comprised of a reference photodiode and a measurement photodiode connected in a transimpedance circuit with dual matched amplifiers, a light source and a difference amplifier means.

19. The structure set forth in claim 17 wherein said differentiation means is comprised of a differential amplifier and associated electronic components.

20. The structure set forth in claim 17 wherein said conditioning means is comprised of amplification means and sample and hold means.

21. The structure set forth in claim 17 wherein said comparison means is comprised of electronic components the output of which is digital.

22. The structure set forth in claim 17 wherein said known threshold level is comprised of the sum of a zero reference level, any deviation around said zero reference level and a predetermined level.

* * * * *